US005793230A

United States Patent [19]
Chu et al.

[11] Patent Number: 5,793,230
[45] Date of Patent: Aug. 11, 1998

[54] SENSOR READOUT DETECTOR CIRCUIT

[75] Inventors: Dahlon D. Chu, Albuquerque, N. Mex.; Donald C. Thelen, Jr., Bozeman, Mont.

[73] Assignee: Sandia Corporation, Albuquerque, N. Mex.

[21] Appl. No.: 806,950

[22] Filed: Feb. 26, 1997

[51] Int. Cl.$^6$ .......................... H03K 5/153; H01L 31/00
[52] U.S. Cl. .......................... 327/77; 327/514; 327/307
[58] Field of Search ............................. 327/77, 78, 79, 327/103, 337, 554, 362, 363, 514, 509, 87, 307; 330/259, 290

[56] References Cited

U.S. PATENT DOCUMENTS

| | | | |
|---|---|---|---|
| 3,659,082 | 4/1972 | Rolfe | 235/150.53 |
| 4,492,931 | 1/1985 | Deweck | 330/294 |
| 4,567,363 | 1/1986 | Goodnough | 250/214 A |
| 4,574,249 | 3/1986 | Williams | 330/59 |
| 4,577,233 | 3/1986 | Kimata | 358/213 |
| 4,647,544 | 3/1987 | Nicoli | 436/518 |
| 4,652,925 | 3/1987 | Kimata | 358/213 |
| 4,658,219 | 4/1987 | Saari | 330/253 |
| 4,697,098 | 9/1987 | Cloke | 327/79 |
| 4,728,828 | 3/1988 | Goodnough | 307/493 |
| 4,819,646 | 4/1989 | Cheung | 128/633 |
| 4,833,418 | 5/1989 | Quintus et al. | 330/259 |
| 4,860,073 | 8/1989 | Michon | 357/24 |
| 4,892,101 | 1/1990 | Cheung | 128/633 |
| 4,928,158 | 5/1990 | Kimata | 357/24 |
| 4,929,923 | 5/1990 | Sato | 330/308 |
| 5,043,820 | 8/1991 | Wyles | 358/213.28 |
| 5,107,103 | 4/1992 | Gruss | 250/208.3 |
| 5,134,276 | 7/1992 | Hobbs | 250/208.2 |
| 5,216,386 | 6/1993 | Wyatt | 330/308 |
| 5,225,888 | 7/1993 | Selwyn | 356/346 |
| 5,245,200 | 9/1993 | Fladda | 250/564 |
| 5,339,303 | 8/1994 | Yoshimaru | 327/77 |
| 5,367,154 | 11/1994 | Pfeiffer | 250/208.1 |
| 5,412,335 | 5/1995 | Jackson | 327/552 |
| 5,471,665 | 11/1995 | Pace et al. | 330/259 |

OTHER PUBLICATIONS

R.J. Wiegerink, E. Seevenck, and W. DeJager, "Offset Cancelling Circuit," *IEEE J. Solid-State Circuits*, vol. 24, pp. 651–658, Jun. 1989.

J.C. Stanton, "A Low Power Low Noise Amplifier for a 128 Channel Detector Read–out Chip," *IEEE Trans. Nucl. Sci.*, vol. 36, pp. 522–527, Feb. 1989.

H. W. Klein and M. E. Robinson, "A 0.8 nV/√Hz CMOS Pre–amplifier for Magneto–resistive Read Elements," *IEEE J. Solid–State Circuits*, vol. 29, pp. 1589–1595, Dec. 1994.

K. Nagaraj, J. Vlach, T. R. Viswanathan, and K. Singhal, "Switched–Capacitor Integrator with Reduced Sensitivity to Amplifier Gain," *Electronics Letters*, vol. 22, pp. 1103–1105, Oct. 1986.

W.H. Ki and G. C. Temes, "Low–Phase–Error Offset–Compensated Switched–Capacitor Integrator," *Electronics Letters*, vol. 26, pp. 957–959m Jun. 1990.

(List continued on next page.)

*Primary Examiner*—Toan Tran

[57] ABSTRACT

A sensor readout detector circuit is disclosed that is capable of detecting sensor signals down to a few nanoamperes or less in a high (microampere) background noise level. The circuit operates at a very low standby power level and is triggerable by a sensor event signal that is above a predetermined threshold level. A plurality of sensor readout detector circuits can be formed on a substrate as an integrated circuit (IC). These circuits can operate to process data from an array of sensors in parallel, with only data from active sensors being processed for digitization and analysis. This allows the IC to operate at a low power level with a high data throughput for the active sensors. The circuit may be used with many different types of sensors, including photodetectors, capacitance sensors, chemically-sensitive sensors or combinations thereof to provide a capability for recording transient events or for recording data for a predetermined period of time following an event trigger. The sensor readout detector circuit has applications for portable or satellite-based sensor systems.

32 Claims, 5 Drawing Sheets

OTHER PUBLICATIONS

J.H. Fischer, "Noise Sources and Calculation Techniques for Switched Capacitor Filters," *IEEE J. Solid–State Circuits*, vol. SC–17, pp. 742–752, Aug. 1982.

K. L. Lee and R. G. Meyer, "Low–Distortion Switched–Capacitor Filter Design Techniques," *IEEE J. Solid–State Circuits*, vol. SC–20, pp. 1103–1113, Dec. 1985.

P.E. Allen and D. R. Holberg, *CMOS Analog Circuit Design*, Published by Holt, Rinehart and Winston, Inc. (New York, 1987) pp. 374–386.

L. Armstrong and L Holyoke, "NASA's Tiny Camera has a Wide–Angle Future," *Business Week*, pp. 54–55, Mar. 6, 1995.

P. Clarke, "RAM–Based Vision Chips on Tap," *Electronic Engineering Times*, pp. 41–42, Jun.12, 1995.

C. Brown, "All–CMOS Imaging Challenges CCDs," *Electronic Engineering Times*, p. 31, Jan. 2, 1996.

D. C. Thelen Jr. and D. D. Chu, "A Low Noise Readout Detector Circuit for Nano–Ampere Sensor Applications," *Proceedings of the IEEE 1996 Custom Integrated Circuits Conference*, pp. 291–294, May 5, 1996.

SENSOR READOUT DETECTOR CIRCUIT

GOVERNMENT RIGHTS

This invention was made with Government support under Contract No. DEAC04-94AL85000 awarded by the U.S. Department of Energy. The Government has certain rights in the invention.

BACKGROUND OF THE INVENTION

1. Field of the Invention (Technical Field)

The present invention relates to a sensor readout detector circuit, preferably in the form of an integrated circuit, that is capable of detecting nano-ampere current signals of interest in high background noise levels. The sensor readout detector circuit can be used in combination with one or more sensors (e.g. light sensors such as photodetectors) to detect and process sensor event signals and to provide a trigger signal to additional circuitry when the sensor event signals are above a predetermined threshold level.

2. Background Art

Biological image systems demonstrate that image processing can be done very efficiently if raw pixel information from a plurality of sensors is processed in parallel with only relevant information being extracted. A biological image system operating in this mode is generally much faster than a digital computer that processes similar image information in a serial manner. Therefore, electronic circuits and methods are needed that mimic the operation of biological systems and provide for the parallel processing of sensor information from a plurality of sensors. This would have an important advantage of reducing the amount of information that a central processing unit (CPU) or computer must process to analyze sensor information of interest.

Most digital optical imaging systems presently in use rely on sensors comprising focal-plane arrays of charge-coupled devices (CCDs). These optical imaging systems sample the charge produced at each pixel (i.e. each individual sensor) at a specified frame rate of, for example, 30 frames per second. Readout circuitry connected to the CCD sensors then measures the total charge at each pixel and generates one or more serial data streams for digitization or analysis. Because of the serial format of data from such CCD optical imaging systems, very high pixel data frame rates of up to about 100 KHz or more are difficult to achieve. Furthermore, the entire CCD focal-plane array must be scanned in a sequential fashion, resulting in a large amount of raw pixel data that must be signal conditioned, digitized, and processed off chip. Since all of the imaging data is read out in a serialized fashion without any thresholding to eliminate data from pixels that are at or near a background noise level (i.e. those pixels not containing information of interest), data processing is relatively inefficient, requiring substantial CPU capacity and resulting in excessive power consumption, especially for portable or satellite-based sensor systems.

U.S. Pat. No. 4,492,931, to Deweck, entitled "Infra-Red Receiver Front End," discloses a voltage-mode transimpedance amplifier which has a high-Q instability resulting from the voltage-mode transimpedance amplifier interacting with parasitic capacitances. U.S. Pat. No. 4,574,249, to Williams, entitled "Nonintegrating Lightwave Receiver," also discloses a voltage-mode transimpedance amplifier with intrinsic high-Q instability. U.S. Pat. No. 5,412,335, to Jackson, et al., entitled "Area-Efficient Current-input Filter, Virtual Ground Circuit Used in Same, and Method Therefor," discloses a current-buffered operational amplifier that is not fully differential as in the present invention.

SUMMARY OF THE INVENTION
(DISCLOSURE OF THE INVENTION)

The present invention is of an apparatus (preferably a sensor readout detector integrated circuit) for and method of detecting nanoampere-level electrical current signals from one or more sensors, comprising: converting by transimpedance amplifier each electrical current signal to a voltage signal; amplifying the voltage signal; removing direct-current (DC) and low-frequency noise components from the voltage signal by a switched capacitor integrator; and detecting signals of interest above a predetermined threshold level by an auto-zeroed comparator. In the preferred embodiment of the present invention, the nanoampere-level electrical current signals are generated by one or more sensors (e.g. photodetectors sensing incident light). Additionally, in the preferred embodiment, the step of converting by transimpedance amplifier is performed by a current-buffered operational amplifier. In the preferred embodiment, the step of amplifying employs a low-pass filter; the step of removing background noise components employs a switched-capacitor integrator having unity gain frequency in the range of about 10–100 Hz and a clock frequency in the range of about 1–10 KHz; and the step of detecting signals of interest employs an auto-zeroed comparator having an adjustable threshold level, and an analog-to-digital converter to digitize signal data.

A primary object of the present invention is the reduction of input referred noise in the readout detector circuit to less than a few hundred picoamperes (pA);

Another object of the invention is the provision of bandpass filtering (e.g. 100 Hz to 30 KHz) of the sensor signal;

Still another object of the invention is to provide a very low standby power requirement of preferably less than 250 microamperes (μA); and Yet another object of the invention is the ability to hold one or more background direct-current (DC) signals (e.g. from an array of photodetectors forming an image) for up to several seconds or more during digitizing of signals of interest.

A primary advantage of the present invention is that input current signals from sensors are continuously processed by the sensor readout detector circuit and only digitized when the input current signals are above a predetermined threshold level.

Another advantage of the invention is use of a fully differential circuit design to provide a high power supply rejection ratio.

Yet other advantages of the present invention are the provision of background substraction and a tunable signal bandpass in the range of about 100 Hz to 30 KHz.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention.

In the drawings.

DETAILED DESCRIPTION OF THE INVENTION

Figure 1:
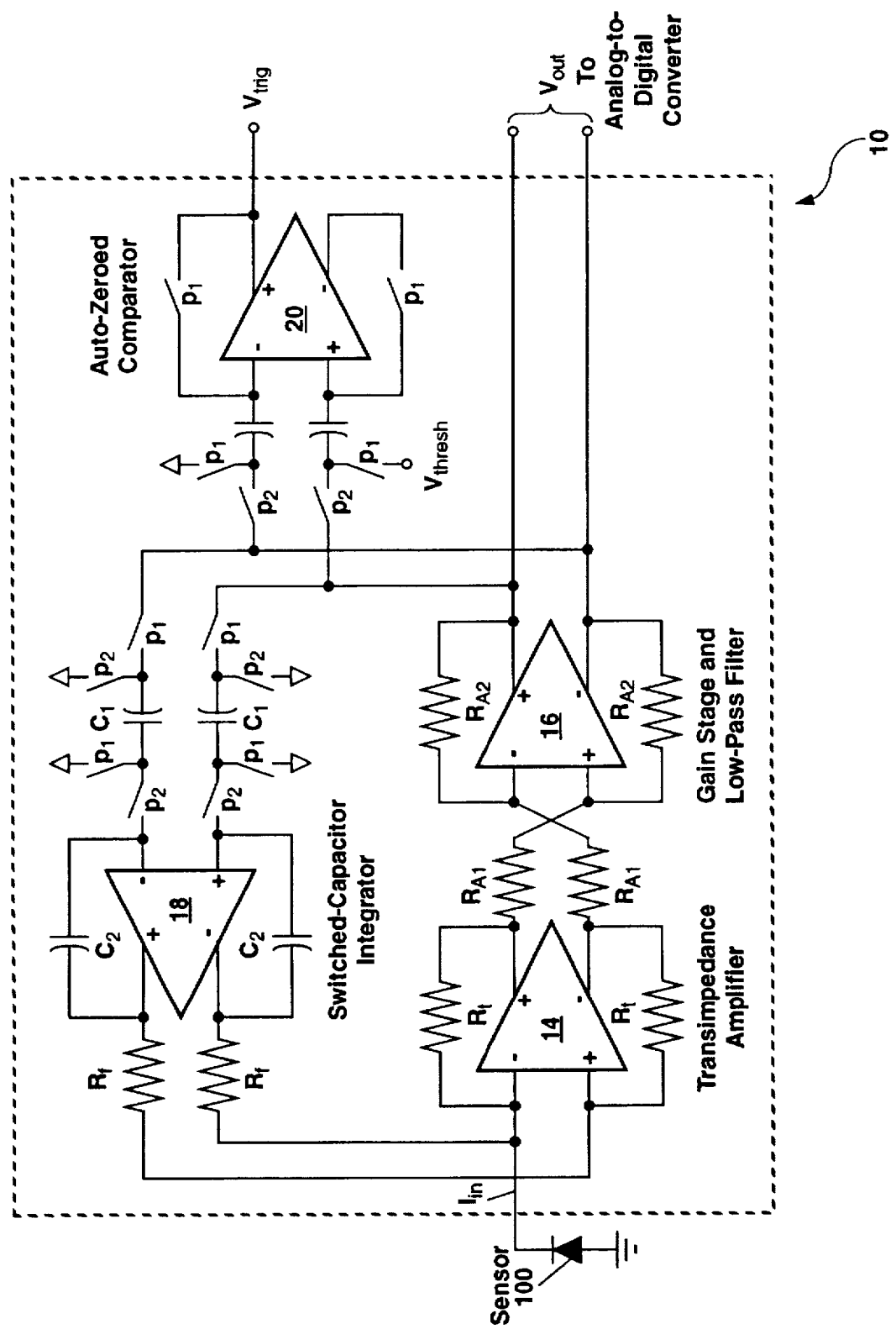
FIG. 1 is a single-channel sensor readout detector circuit according to the present invention.

FIG. 1 shows a block circuit diagram of an embodiment of a single-channel sensor readout detector circuit 10 according to the present invention. A plurality of single-channel sensor readout detector circuits 10 can be formed on a common substrate as an integrated circuit (IC). Such a readout detector IC can be used for processing signals generated by a plurality of sensors 100 such as photodetectors (including an array of photodiodes or an array of charge-coupled devices), capacitive sensors, or chemically-sensitive sensors (e.g. chemfets) that, in some instances, can be included on the substrate. The term photodetector as used herein refers to any type of sensor for detecting electromagnetic radiation, including photodiodes and charge-coupled devices.

In FIG. 1, the sensor readout detector circuit 10 comprises a transimpedance amplifier 14 for receiving an input current signal from a sensor 100 and converting the input current signal to a voltage signal; a gain stage 16 connected to outputs of the transimpedance amplifier 14 for amplifying (and preferably also low-pass filtering) the voltage signal to provide an amplified voltage signal; a switched-capacitor integrator 18 in a feedback configuration for receiving the amplified voltage signal and feeding direct-current (DC) and low-frequency (<100 Hz) noise components back to the input of the transimpedance amplifier 14 to substantially remove these DC and low-frequency noise components from the amplified voltage signal.

An auto-zeroed comparator 20 having an adjustable input threshold level is connected to outputs of the gain stage 16 for detecting signals of interest in the amplified voltage signal by reference to an input threshold voltage, $V_{thresh}$. The auto-zeroed comparator 20 provides a trigger output voltage, $V_{trig}$, than can be used to signal an analog-to-digital converter (not shown) for digitizing the signals of interest.

In FIG. 1, the switched-capacitor integrator 18 can operate in either an offset-cancelling mode or in a differential mode with mutually exclusive operation of switches $p_1$ and $p_2$ (e.g. formed from n-channel transistors) controlled by a clock. To keep the integrator transfer function valid with continuous feedback through the transimpedance amplifier 14 and the gain stage 16, the integrator should not have a continuous path between its input and output. This can be achieved by delaying the integrator input by one or more clock cycles, which corresponds to a forward Euler configuration. The integrator 18 should preferably be configured to provide a low input offset voltage as compared to the threshold voltage, $V_{thresh}$, of the auto-zeroed comparator 20. The configuration of the switched-capacitor integrator 18 can also include additional capacitors (not shown in FIG. 1) for glitch suppression.

The switched-capacitor integrator 18 is preferably clocked at a clock frequency of about 1–10 KHz when the circuit 10 is in the form of an integrated circuit (IC) to keep the capacitor ratios $C_2:C_1$ small (16:1). The clock can be further skewed up to a 99% duty cycle to maximize the time that the circuit 10 looks for signals of interest.

Tripping the auto-zeroed comparator 20 by a signal of interest above the threshold level turns off the clock to the switched-capacitor integrator 18, causing the integrator to hold its value for a predetermined period of time. This permits the analog-to-digital converter to digitize data (i.e. the signals of interest) from the sensor 100 without background updates. It should be noted that the integrator 18 will not alias signals being fed to the analog-to-digital converter during the time the clock has been disabled.

Since the clock is turned off when the auto-zeroed comparator 20 is tripped, there are two transfer functions for the sensor readout detector circuit 10. For low-frequency (<100 Hz) background signals from the sensor 100 having an amplified signal voltage level of less than $V_{thresh}$, the circuit 10 is clocked to operate as a sampled data circuit with a first transfer function from the sensor 100 input current, $I_{in}$, to the amplified output voltage, $V_{out}$, given by:

$$\frac{V_{out}}{I_{in}} = AR_t \frac{z-1}{z-1+A\left(\frac{C_1}{C_2}\right)\left(\frac{R_t}{R_f}\right)}$$

where $R_t$, $R_f$, $C_1$ and $C_2$ are indicated in the circuit diagram of FIG. 1, and A is the signal gain of gain stage 16 determined by resistors, $R_{A1}$ and $R_{A2}$. The first transfer function has a zero at a DC signal level (i.e. z=1) which serves to subtract any background signal level (e.g. due to ambient illumination of a photodetector sensor 100), including any background noise with a frequency below 100 Hz. This background subtraction is advantageous for monitoring time-varying sensor signals at frequencies above 100 Hz that can be up to orders of magnitude smaller than a total background signal level from the sensor 100. During this background subtraction mode of operation, the feedback loop in the circuit 10 is stable when the circuit elements $R_t$, $R_f$, $C_1$ and $C_2$ and the gain, A, are selected to provide:

$$0 < A\left(\frac{C_1}{C_2}\right)\left(\frac{R_t}{R_f}\right) < 2$$

In a preferred embodiment of the present invention, A=10, $R_t=R_f=400$ k$\Omega$. In this preferred embodiment, the switched-capacitor integrator 18 can have a unity gain frequency of 10 Hz by using $C_1=1$ pF and $C_2=16$ pF and a 1 KHz sampling clock frequency. These component values set a high-pass pole for the circuit feedback loop to be at 100 Hz. The use of a 1 KHz clock frequency keeps the capacitor ratio $C_1:C_2$ small. The 1 KHz clock can also be skewed to provide a 99% duty cycle to maximize the time that the circuit 10 is looking for signals of interest from the sensor 100. In other embodiments of the present invention, the unity gain frequency of the circuit 100 can be in the range of about 10–100 Hz, and the clock frequency can be in the range of about 1–10 KHz.

Once a signal of interest has been detected by the auto-zeroed comparator, the clock is stopped by an output signal, $V_{trig}$, from the auto-zeroed comparator 20, and the background subtraction (i.e. the feedback from the switched-capacitor integrator 18) is fixed at its level immediately before the detection of the signal of interest. The circuit 10 then operates for a predetermined period of time to continuously pass the signal of interest (with the background signal level subtracted) and feed the signal of interest to the analog-to-digital converter with a second transfer function given by:

$$\frac{V_{out}}{I_{in}} = AR_f \frac{\omega}{s+\omega}$$

where ω=2πf, and f is an upper roll-off frequency of the gain stage 16 (generally selected to be about 20–30 KHz). In this mode of operation, the signal of interest is amplified to provide an output voltage, $V_{out}$, that can be measured differentially and digitized by an analog-to-digital converter. This mode of operation of the circuit 10 is advantageous in that only relevant data (i.e. signals of interest above a predetermined threshold level) is sent to the analog-to-digital converter and subsequently stored, processed or otherwise analyzed, thereby minimizing CPU requirements and power consumption. Moreover, since each sensor 100 is provided with a different sensor readout detector circuit 10, data from each sensor 100 is sensed and processed in parallel to provide a high bandwidth for sensor data transfer, with nearly a 100% duty an cycle.

In FIG. 1, the sensor readout detector circuit 10 can be formed with the transimpedance amplifier 14 comprising a high-gain low-noise operational amplifier M(e.g. a CMOS amplifier) having differentially-paired transistors and feedback resistors, $R_f$. For such a transimpedance amplifier 14, the input referred current noise associated with feedback resistors, $R_f$, is about three orders of magnitude smaller than the noise from the operational amplifier. Therefore, the dominant noise source of the amplifier 14 is the input referred voltage noise of the operational amplifier divided by the value, $R_f$, of the feedback resistors. Providing the transimpedance amplifier 14 with a low value of input referred thermal noise requires that each differential pair of transistors have a large ratio of gate width (W) to gate length (L) and a large bias current, and that current mirror transistors in the operational amplifier of the transimpedance amplifier 14 have a small W/L ratio.

Figure 2:
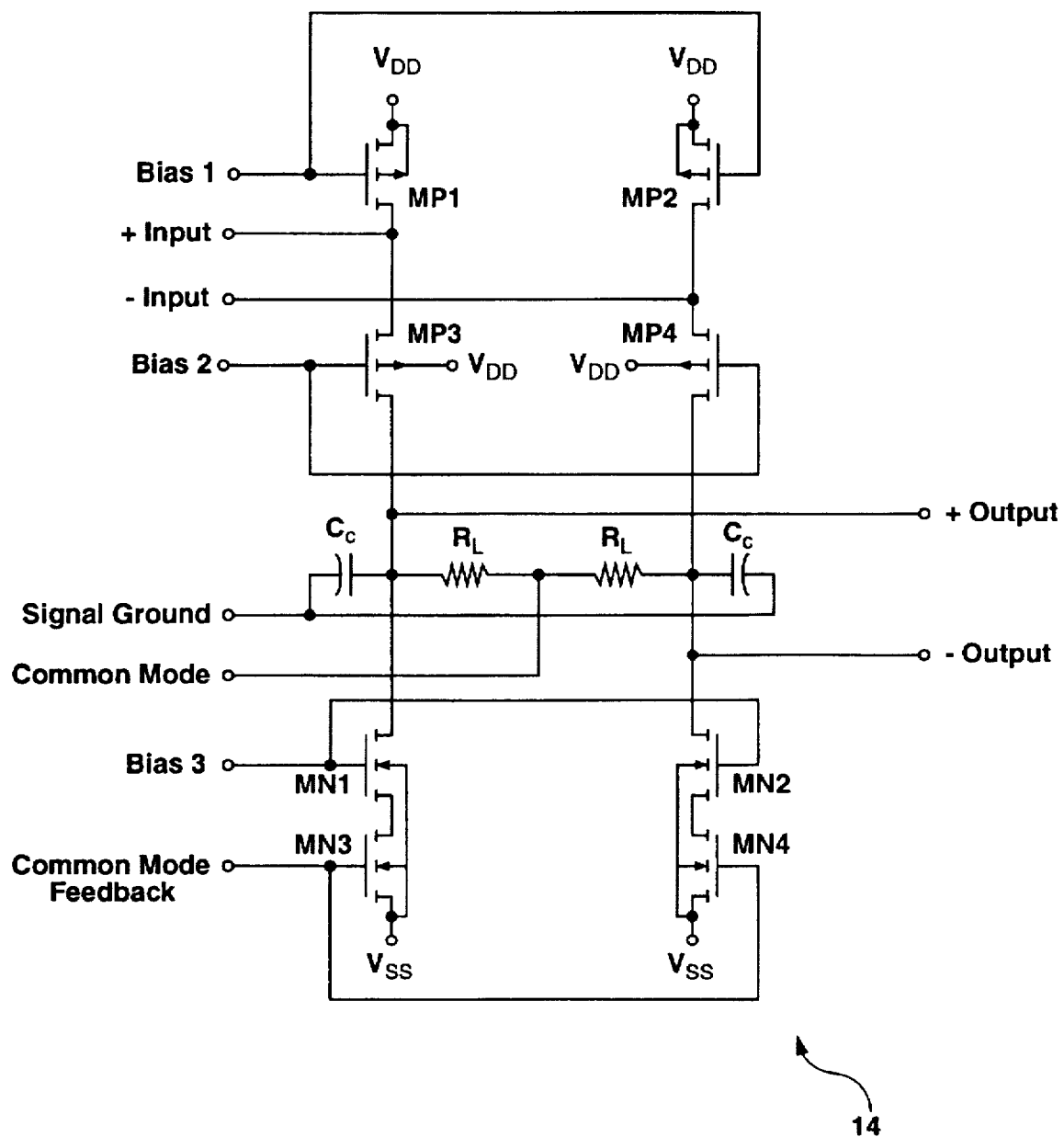
FIG. 2 is a schematic diagram of an improved current-buffered transimpedance amplifier 14 that can be used in the sensor readout detector circuit of FIG. 1.

A preferred embodiment of the transimpedance amplifier 14 that is suitable for formation as an integrated circuit (IC) with improved noise performance stability and a reduced power consumption is a current-buffered transimpedance 14 amplifier as shown in FIG. 2.

Formation of the sensor readout circuit 10 as an IC is preferably performed by using low-noise input stages and high-gain fully-differential complementary metal-oxide semiconductor (CMOS) circuitry for the transimpedance amplifier 14, gain stage 16, switch-capacitor integrator 18 and auto-zeroed comparator 20. Differential circuitry is advantageous for improving power supply rejection and also cross-talk rejection. A differential switched-capacitor integrator 18 provides an increased signal-to-noise ratio as compared with a single-ended switched-capacitor integrator (by a factor of the square root of 2 assuming equal-sized capacitors for each of $C_1$ and $C_2$); and the differential integrator 18 further provides a capability to hold the background signal level for up to several seconds or longer. Any leakage on switches, $p_2$, in FIG. 1 appears as a common mode signal and can be rejected by a common-mode feedback circuit (not shown) connected to the switched-capacitor integrator 18. Special care can also be taken to keep any voltage drops from power supply currents off the IC substrate.

In FIG. 2, the transimpedance amplifier 14 is a current-buffered amplifier lacking a differential pair of transistors and feedback resistors. Positive and negative inputs are provided to the source of cascode transistors MP3 and MP4, respectively, with transistors MP1 and MP2 forming current sources. The input resistance is approximately the inverse of the transconductance ($g_m^{-1}$) for transistors MP3 or MP4. Since the drain current and source currents of a metal-oxide-semiconductor field-effect transistor (MOSFET) are equal, an electrical current provided to the positive input of the current-buffered transimpedance amplifier 14 flows to the drain of transistor MN1 and to the output resistors, $R_L$ (which in a preferred embodiment are 400 kΩ, with capacitors, $C_c$, being 1.5 pf). The current flowing through transistors MN3 and MN4 is further controlled by a common-mode feedback amplifier (not shown) connected between a common mode node and a common mode feedback node in FIG. 2. For a single-ended input, the common-mode feedback amplifier should preferably have a high DC gain to maintain a small common-mode voltage at the differential output of the current-buffered transimpedance amplifier 14.

In the sensor readout detector circuit 10, noise arises from the resistors, from operational amplifiers in the gain stage 16 and integrator 18, from the transimpedance amplifier 14, and from the switches. During the time that the clock is stopped for data acquisition of the sensor signal, there is a continuous transfer function from each of these noise sources to the amplified output voltage, $V_{out}$. The most significant sources of noise are from the operational amplifiers and the transimpedance amplifier 14.

In FIG. 2, the input referred current noise of the current-buffered transimpedance amplifier 14 is dominated by the mean square sum of the current noise in transistors MP1, MP2, MN3, and MN4. A thermal noise current in the amplifier 14 is proportional to $g_m$ of the above transistors, so the drain current and the W/L ratio of these transistors can both be made small to minimize thermal noise. To minimize flicker noise from the transimpedance amplifier 14, the channel lengths of MP1, MP2, MN3, and MN4 can be made long, with their drain currents being made small. Therefore, optimizing noise performance in the transimpedance amplifier 14 also complements efforts to minimize area and power consumption of the circuit 10 to fit a plurality of sensor readout detector circuits 10 onto a common IC chip.

However, there is a trade-off with having too small of a bias current in the current buffer. If the input current coming out of the positive (+) input exceeds the bias current sourced from MP1, the input current signal will be clipped. Additionally, it is generally desirable to minimize the input impedance of the current buffer in the transimpedance amplifier 14, but a large bias current cannot be used to accomplish this. A small input impedance can be achieved by increasing the $g_m$ of transistor MP3 by making its W/L large. In the case of a unidirectional input current (e.g. from a photodetector sensor 100 that senses light), an input stage of the transimpedance amplifier 14 can be used in a class AB fashion. Current coming into the positive input will then increase the $V_{gs}$ of MP3, and can be much larger than the bias current without causing clipping. The input impedance of the transimpedance amplifier 14 can also be lowered by replacing transistors MP3 and MP4 with a regulated gate cascode configuration, thereby allowing even more current to flow into the input without clipping. Another benefit of the current buffer is the lack of a complex pole caused by a parasitic input capacitance.

Unwanted signals can be added to the signal of interest from a sensor 100 when a plurality of sensor readout detector circuits 10 are formed on a chip or substrate. Signals from neighboring circuits 10 can couple through the power supplies, the substrate, and from parallel or overlapping interconnects onto sensitive nodes such as the transimpedance amplifier inputs. Capacitive coupling from parallel and overlapping interconnections can be avoided by careful IC layout, and by shielding of sensitive nodes. Differential circuits can also be used to reject cross talk through the power supplies. A separate power supply connected only to the substrate can keep voltage drops on the main supply lines from modulating the substrate and causing cross talk. Because input pads to the IC chip have a low impedance, any voltage swings induced thereon will be small, and minimal coupling between neighboring sensor readout detector circuits 10 will occur. Close attention can also be paid to cell and chip layouts using matched- and common-centroid layout techniques to reduce input offsets.

An ability to hold the background level substantially constant for a time period of up to several seconds or more can be achieved with a differential switched-capacitor integrator 18. While the integrator 18 is holding the background current, any leakage current on switches between the sampling capacitor, $C_1$, and the operational amplifier in the integrator 18 will appear as a common mode signal, and can be rejected by a common mode feedback circuit (not shown). Charge injection can also be reduced to a common mode signal by using a delayed clock on the switches where a gate-to-source voltage on the transistor switch is input signal voltage dependent.

Figure 3:
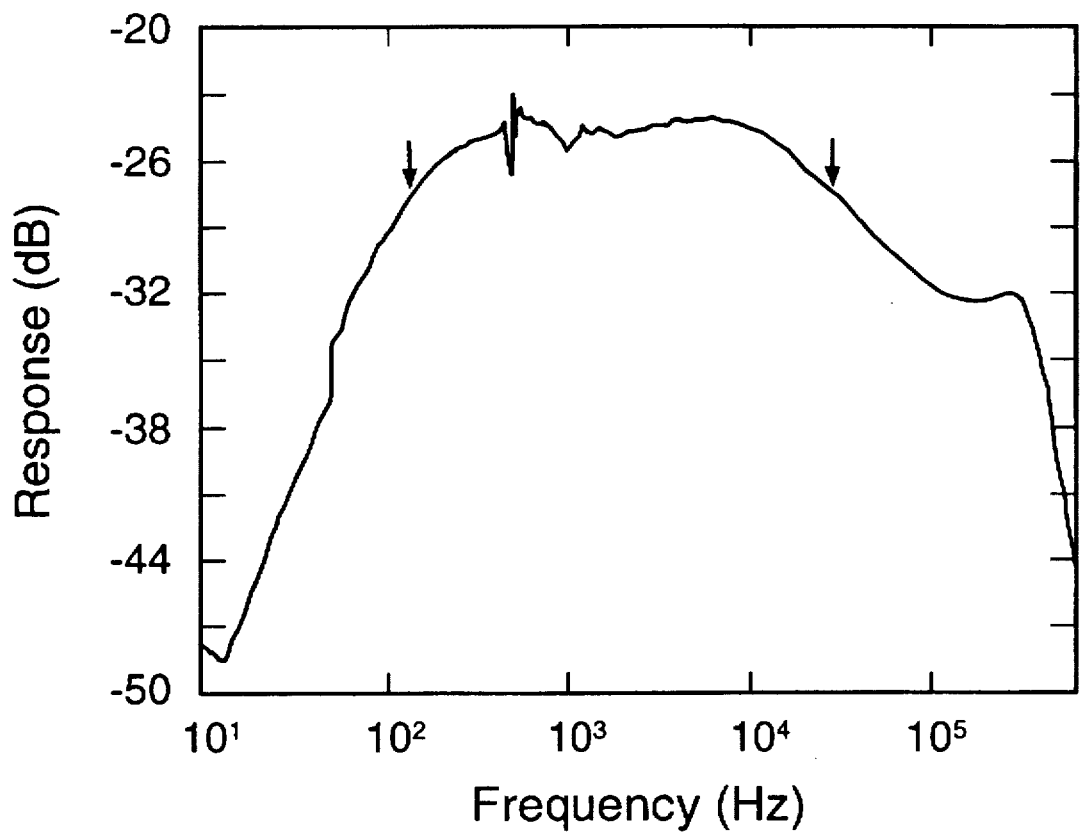
FIG. 3 is a diagram of frequency response of the sensor readout detector circuit of FIG. 1 in IC form.

FIG. 3 shows the frequency response of the sensor readout detector circuit 10 measured using a spectrum/network analyzer (Hewlett-Packard, Model 3589A). In FIG. 3, a bandpass filter response is seen with −3 dB high- and low-pass corner frequencies at 150 Hz and 35 KHz, respectively (as indicated by vertical arrows). The flatband response shown is at about −24 dB because a voltage signal from the spectrum/network analyzer is divided by a 1.2 MΩ resistor to generate a current input signal for the sensor readout detector circuit 10.

Figure 4:
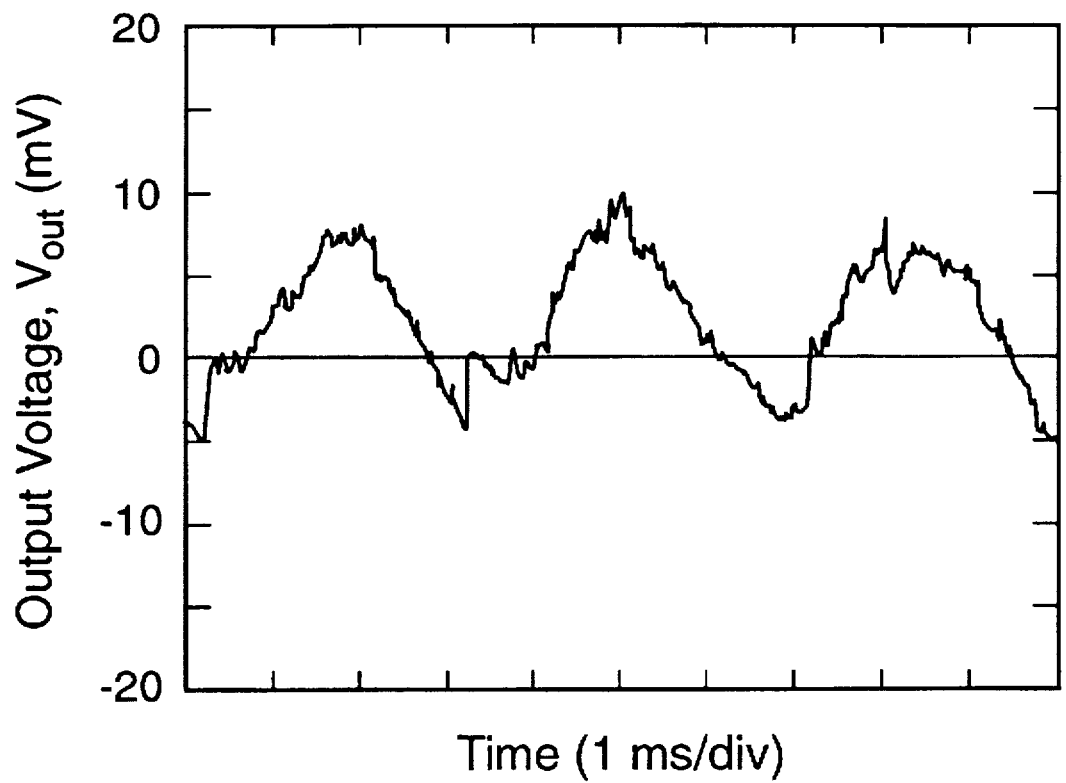
FIG. 4 is an output signal voltage response of the sensor readout detector circuit of FIG. 1 in IC form for a composite input current signal comprising a 4 nA input sinusoid superimposed on a 1 µA DC background level.

FIG. 4 shows the output voltage, $V_{out}$, measured across the two output terminals of the gain stage 16 in response to a composite input signal that comprises a 4 nA, 300 Hz sinusoidal signal component superimposed on a 1 μA DC background level. Note that the sensor readout detector circuit 10 is effective in filtering out the DC background level to provide an output signal that tracks the sinusoidal component of the input signal. FIG. 4 shows the effectiveness of the sensor readout detector circuit 10 of the present invention in removing the large DC noise component (e.g. due to ambient background illumination in a photodetector sensor 100) from a sensor input signal so that a much smaller time-varying sensor signal can be measured. The graininess of the output voltage in FIG. 4 is due to the small size of the sinusoidal component of the composite input signal, and to system noise arising in the circuit 10.

Figure 5A:
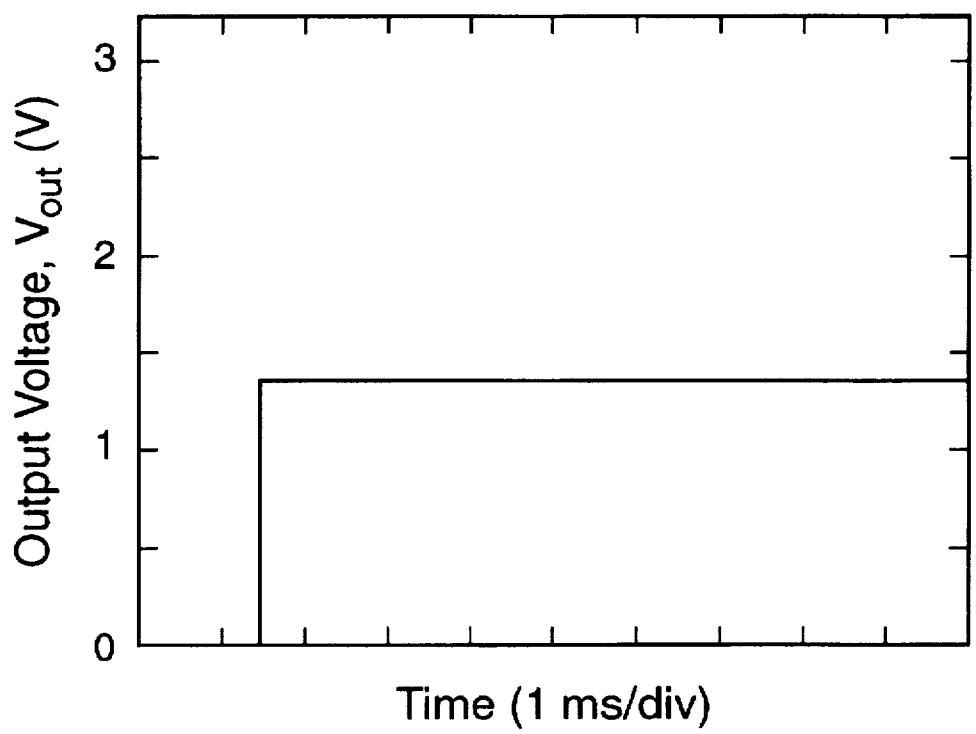
FIGS. 5A and 5b show, respectively, an input step signal to the sensor readout detector circuit of FIG. 1 in IC form and the resultant step response.
Figure 5B:
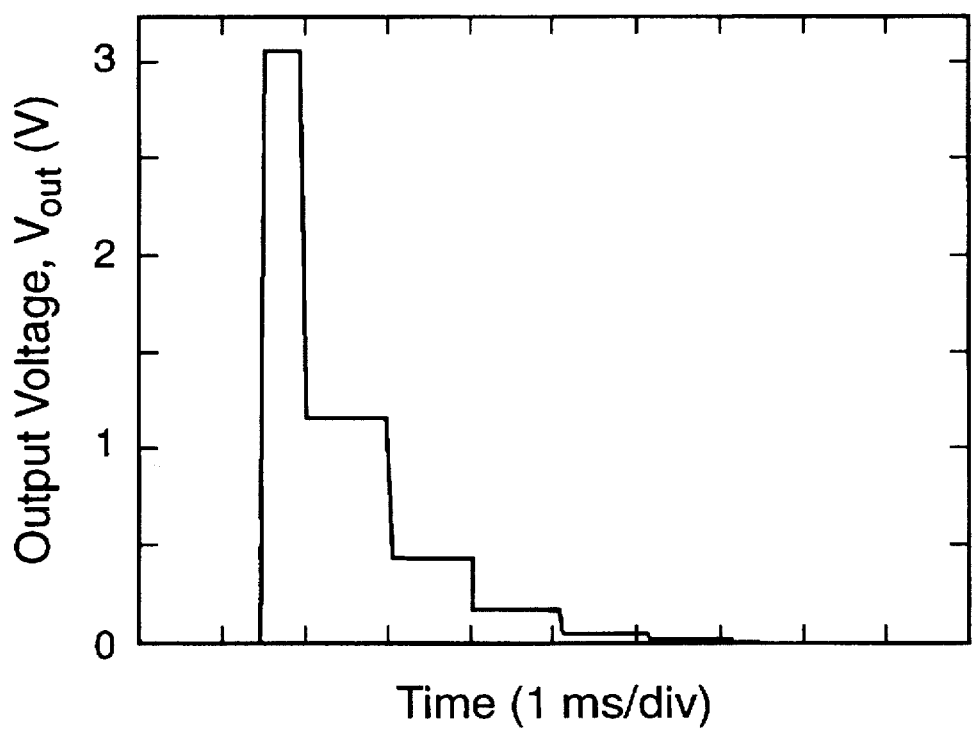

FIGS. 5A and 5B show an input step waveform applied to the sensor input of the sensor readout detector circuit 10 and the resultant output voltage, $V_{out}$. The sensor input in FIG. 5A is a 1.36 volt step into a 110 KΩ resistor to provide a 12.4 μA current step.

In FIG. 5B, the output voltage of the circuit 10 responds within a few clock cycles to remove substantially all of the DC component of the step input. Before the first clock cycle, the output voltage responds to the step input due to the continuous path from the sensor input to the output of the circuit 10. At the first clock cycle, about ⅔ of the DC background is subtracted, and more of the DC background is subtracted with each successive cycle of the 1 kHz clock. The DC background decreases substantially to zero within about 8 milliseconds (5 time constants) of the onset of the step input, corresponding to a 100 Hz high-pass pole of the circuit 10.

The measurements shown in FIGS. 3–5 were made using a sensor readout detector circuit 10 formed as an IC chip fabricated using a 2 μm p-well process. Additional circuits 10 have also been fabricated in IC form with a 1.2 μm n-well process.

Although the invention has been described in detail with particular reference to these preferred embodiments, other embodiments can achieve the same or similar results. The sensor readout detector circuit 10 can be tailored for use with many different types of sensors 100, including photodetectors, capacitance sensors, chemically-sensitive sensors, or combinations thereof. Usage of the circuit 10 with additional types of sensors will become evident to those skilled in the art upon practice of the present invention. The actual scope of the invention is intended to be defined in the following claims when viewed in their proper perspective based on the prior art.

What is claimed is:

1. A readout detector circuit for processing an electrical current signal from at least one sensor, comprising:
   (a) means for receiving the electrical current signal from each sensor and converting the electrical signal to a voltage signal;
   (b) means for amplifying the voltage signal;
   (c) means, connected between the amplifying means and the receiving means, for receiving the amplified voltage signal and removing direct-current and low-frequency noise components from the amplified voltage signal; and
   (d) means for receiving the amplified voltage signal and detecting signals of interest above a predetermined threshold level.

2. The readout detector circuit in claim 1 wherein the means for converting the electrical current signal to a voltage signal comprises a transimpedance amplifier.

3. The readout detector circuit in claim 2 wherein the transimpedance amplifier comprises a current-buffered transimpedance amplifier.

4. The readout detector circuit in claim 1 wherein the means for amplifying the voltage signal includes means for low-pass filtering the voltage signal.

5. The readout detector circuit in claim 1 wherein the means for removing direct-current and low-frequency noise components from the voltage signal comprises a switched-capacitor integrator.

6. The readout detector circuit in claim 5 wherein the switched-capacitor integrator is an offset-cancelling or differential switched-capacitor integrator.

7. The readout detector circuit in claim 5 wherein the switched-capacitor integrator has a unity gain frequency in the range of 10–100 Hz and is clocked at a frequency in the range of 1–10 KHz.

8. The readout detector circuit in claim 1 wherein the means for detecting signals of interest above a predetermined threshold level includes an auto-zeroed comparator having an adjustable input threshold level.

9. The readout detector circuit in claim 8 wherein the means for detecting signals of interest above a predetermined threshold level provides output signals to an analog-to-digital converter only when the signals of interest are above the threshold level.

10. The readout detector circuit in claim 1 wherein the sensors are selected from the group consisting of photodetectors, capacitance sensors, chemically-sensitive sensors, or combinations thereof.

11. The readout detector circuit in claim 1 in the form of an integrated circuit.

12. The readout detector circuit in claim 11 wherein the integrated circuit further includes the at least one sensor.

13. The readout detector circuit in claim 12 wherein the sensors are selected from the group consisting of photodetectors, capacitance sensors, chemically-sensitive sensors, or combinations thereof.

14. A readout detector circuit for processing an electrical current signal from at least one sensor, comprising:

(a) a transimpedance amplifier for converting the electrical current signal to a voltage signal;

(b) a voltage amplifier for amplifying the voltage signal;

(c) a switched capacitor integrator for providing feedback from the voltage amplifier to the transimpedance amplifier for removing direct-current and low-frequency noise components from the voltage signal; and (d) an auto-zeroed comparator for providing an indication when the amplified voltage signal is above a predetermined threshold level.

15. The readout detector circuit of claim 14 wherein the transimpedance amplifier comprises a current-buffered transimpedance amplifier.

16. The readout detector circuit of claim 15 wherein the current-buffered transimpedance amplifier lacks a differential pair and feedback resistors.

17. The readout detector circuit of claim 14 wherein the voltage amplifier includes a low-pass filter.

18. The readout detector circuit of claim 14 wherein the switched capacitor integrator is an offset-cancelling or differential switched-capacitor integrator.

19. The readout detector circuit of claim 14 wherein the switched capacitor integrator has a unity gain frequency in the range of 10–100 Hz and is clocked at a frequency in the range of 1–10 KHz.

20. The readout detector circuit of claim 14 wherein the auto-zeroed comparator includes an adjustable threshold level.

21. The readout detector circuit of claim 14 wherein the auto-zeroed comparator is operatively connected to signal an analog-to-digital converter to digitize signal data.

22. The readout detector circuit of claim 14 in the form of an integrated circuit.

23. The readout detector circuit in claim 22 wherein the integrated circuit further includes the at least one sensor.

24. A method of detecting signals of interest from at least one sensor, the method comprising the steps of:

(a) converting by transimpedance amplifier an electrical current signal from each sensor to a voltage signal;

(b) amplifying the voltage signal;

(c) removing direct-current and low-frequency noise components from the voltage signal by integrating the amplified voltage signal and feeding back the integrated signal to the transimpedance amplifier; and (d) detecting signals of interest by an auto-zeroed comparator.

25. The method of claim 24 wherein the converting step comprises converting by an operational amplifier.

26. The method of claim 24 wherein the converting step comprises converting by a current-buffered transimpedance amplifier lacking a differential pair and feedback resistors.

27. The method of claim 24 wherein the amplifying step further includes a step of low-pass filtering the voltage signal.

28. The method of claim 25 wherein the amplifying step comprises utilizing a unity gain frequency in the range of 10–100 Hz.

29. The method of claim 24 wherein the removing step comprises clocking at 1–10 KHz.

30. The method of claim 29 wherein the removing step comprises a step of stopping the clocking for a predetermined period of time upon detecting signals of interest.

31. The method of claim 30 wherein the step of stopping the clock for a predetermined time upon detecting signals of interest results in holding the integrated signals in the removing step at a substantially constant level for the predetermined period of time.

32. The method of claim 24 wherein the detecting step comprises providing an adjustable threshold level to the auto-zeroed comparator, and further includes a step of digitizing the signals of interest by an analog-to-digital converter.

* * * * *